(12) United States Patent
Bernier

(10) Patent No.: US 12,325,991 B2
(45) Date of Patent: Jun. 10, 2025

(54) HAND-HELD SANITARY DEVICE AND PERSONAL-HYGIENE SACHET FOR WASHING AND DRYING INTIMATE BODY PARTS

(71) Applicant: Gilbert Bernier, Joue les Tours (FR)

(72) Inventor: Gilbert Bernier, Joue les Tours (FR)

( * ) Notice: Subject to any disclaimer, the term of this patent is extended or adjusted under 35 U.S.C. 154(b) by 449 days.

(21) Appl. No.: 17/785,814

(22) PCT Filed: Dec. 14, 2020

(86) PCT No.: PCT/FR2020/000273
§ 371 (c)(1),
(2) Date: Jun. 15, 2022

(87) PCT Pub. No.: WO2021/123515
PCT Pub. Date: Jun. 24, 2021

(65) Prior Publication Data
US 2022/0403639 A1  Dec. 22, 2022

(30) Foreign Application Priority Data

Dec. 16, 2019 (FR) .......................................... 1914477
Nov. 19, 2020 (FR) .......................................... 2011895

(51) Int. Cl.
*E03D 9/08* (2006.01)
*A47K 10/48* (2006.01)
(Continued)

(52) U.S. Cl.
CPC .............. *E03D 9/085* (2013.01); *A47K 10/48* (2013.01); *A61H 19/44* (2013.01); *A61H 33/005* (2013.01);
(Continued)

(58) Field of Classification Search
CPC ... E03D 9/085; A61M 3/0258; A61M 3/0262; A61M 3/025; A47K 7/08; A47K 7/046
See application file for complete search history.

(56) References Cited

U.S. PATENT DOCUMENTS 3,667,461 A * 6/1972 Zamarra ............. A61M 3/0262
604/212
4,622,704 A * 11/1986 Chung .................... E03D 9/085
392/447
(Continued)

FOREIGN PATENT DOCUMENTS

KR   20-2012-0005868      8/2012

OTHER PUBLICATIONS

Search Report and Written Opinion for FR Application No. 1914477 dated Aug. 3, 2020, 8 pages (with English Translation).
(Continued)

*Primary Examiner* — Janie M Loeppke
(74) *Attorney, Agent, or Firm* — NIXON & VANDERHYE

(57) ABSTRACT

Disclosed is a hand-held sanitary device and to an impermeable and essentially biodegradable personal-hygiene sachet which can be filled with water and used for washing intimate body parts by gentle rubbing. The sanitary device chiefly includes a stop piece, a ring, a spring for keeping the personal-hygiene sachet sealed, a valve and connection to a water heater and dryer which is controlled by the valve. It can be used with running-water toilet bowls, without the need to use toilet paper. The sanitary device is particularly intended for the surface washing of intimate body parts, for vaginal washing, re-establishing pelvic-floor muscle tone, and pleasurable vaginal stimulation in women, using the hygienic sachet intended for each use.

6 Claims, 4 Drawing Sheets

(51) Int. Cl.
  *A61H 19/00* (2006.01)
  *A61H 33/00* (2006.01)
  *A61H 35/00* (2006.01)

(52) U.S. Cl.
  CPC ..... *A61H 33/0095* (2013.01); *A61H 33/6068* (2013.01); *A61H 35/00* (2013.01); *A61H 2201/0153* (2013.01); *A61H 2201/0157* (2013.01); *A61H 2201/0207* (2013.01); *A61H 2201/025* (2013.01); *A61H 2205/087* (2013.01)

(56) References Cited

U.S. PATENT DOCUMENTS

| | | | | |
|---|---|---|---|---|
| 5,991,937 A | * | 11/1999 | Safara | E03D 9/085 239/315 |
| 2007/0000041 A1 | | 1/2007 | Masuda | |
| 2010/0312199 A1 | * | 12/2010 | Lu | A47K 7/08 604/279 |
| 2012/0297529 A1 | * | 11/2012 | Bowcutt | A61M 3/0262 4/448 |
| 2013/0014340 A1 | * | 1/2013 | Ottah | A47K 7/08 15/320 |

OTHER PUBLICATIONS

Search Report and Written Opinion for FR Application No. 2011895 dated Mar. 26, 2021, 11 pages (with English Translation).
International Search Report and Written Opinion of the ISA for PCT/FR2020/000273 dated May 4, 2021, 13 pages (with English Translation).

* cited by examiner 15        17 18

16

HAND-HELD SANITARY DEVICE AND PERSONAL-HYGIENE SACHET FOR WASHING AND DRYING INTIMATE BODY PARTS

CROSS-REFERENCE TO RELATED APPLICATIONS

This application is the U.S. national phase of International Application No. PCT/FR2020/000273 filed Dec. 14, 2020 which designated the U.S. and claims priority to FR Patent Application No. 1914477 filed Dec. 16, 2019, and FR Patent Application No. 2011895 filed Nov. 19, 2020, the entire contents of each of which are hereby incorporated by reference.

BACKGROUND OF THE INVENTION

Field of the Invention

The present invention relates to a hand-held sanitary device and a single-use sanitary bag for washing intimate body parts by gentle rubbing and drying them with hot air.

Description of the Related Art

Devices for washing intimate body parts are known, such as water ejectors installed in toilet bowls and hand-held shower heads. The disadvantage of these devices is the difficulty for the user to avoid splashing while using a jet of water that suffices to reach his intimate body part that needs to be washed, especially his perianal area after defecation.

SUMMARY OF THE INVENTION

The present invention remedies this disadvantage by providing a hand-held sanitary device that makes it possible to use a sanitary bag that is filled with water and stretched for the surface washing of intimate body parts by gentle rubbing. The device is convenient to use in order to be able to rub gently with precision the intimate body part that must be washed, in particular the perianal area after defecation, without wetting the other parts of the body or splashes. It thus allows a satisfactory washing of the intimate body parts with a light water flow and a short hot air drying time. It can be used with the current toilet bowls and without the need to use toilet paper, the manufacturing of which is among the causes of deforestation in the world.

An apparatus for heating water and generating a hot air flow is provided and may be considered as an instantaneous water heater and dryer.

A water container and a washing bulb with female threads that allow them to be screwed onto the sanitary device for portable use are provided.

Particular and advantageous embodiments of the invention are set forth below and described in detail below.

According to an embodiment, the sanitary device makes it possible to use a sanitary bag filled with water and stretched for the surface washing of intimate body parts by gentle rubbing. It includes a conical stop with a ring that is subjected to the action of a compression spring for a tight holding of a single-use sanitary bag, a valve for controlling the flow of water, a thread for coupling to a water supply hose, a water passage, a water outlet and an open ring for holding a hot air supply hose. The sanitary bag has a water outlet that is covered with a band which allows to avoid splashes and a cylindrical part with a lateral opening which allows to direct the flow of hot air toward the intimate body parts by conveniently holding the sanitary device with one hand during drying. This device can also be used for vaginal washing, perineal rehabilitation and women's vaginal pleasure using the sanitary bag provided for each use. In another embodiment, the sanitary device includes a smooth end intended to be covered with an impermeable sanitary bag and to be used for rubbing the intimate body parts during washing. A clip that holds this bag is provided on the body of the device. In yet another embodiment, the sanitary device has a smooth foldable end and is easy to carry during travel. It is intended for the surface washing of intimate body parts. The sanitary bags provided for the various uses according to the invention are made of an impermeable, essentially biodegradable and compostable material. They are single-use and can be marketed in closed pouches of one or a few sanitary bags or possibly in the form of rolls of pre-cut sanitary bags. They can be transparent or opaque.

The instantaneous water heater and dryer includes a resistor mounted around a water pipe, which constitutes the main part of the instantaneous water heater, a second resistor with a small fan, which constitutes the main part of the dryer, protections against overheating, switches, a pressure reducer which allows to limit the water pressure in the water supply hose and in the sanitary bag which is intended to be filled with water and used for rubbing intimate body parts during washing, a timer that allows to set the operating time of the dryer after each wash, a pressure switch with an electric change-over contact that allows to switch the power supply between the instantaneous water heater and the dryer by opening and closing the water flow control valve, a water inlet, a hot water outlet, an air inlet and a hot air outlet. The change-over contact of the pressure switch has a normally open contact, a normally closed contact and a common contact between the two. The timer has two terminals for the connection of its power supply and a normally closed contact that opens after the preset time. This time is counted from the moment it is switched on.

BRIEF DESCRIPTION OF THE DRAWINGS

Further features and advantages of the invention will be apparent from the following description of non-limiting examples with reference to the attached drawings in which.

DESCRIPTION OF THE PREFERRED EMBODIMENTS

Figure 1:
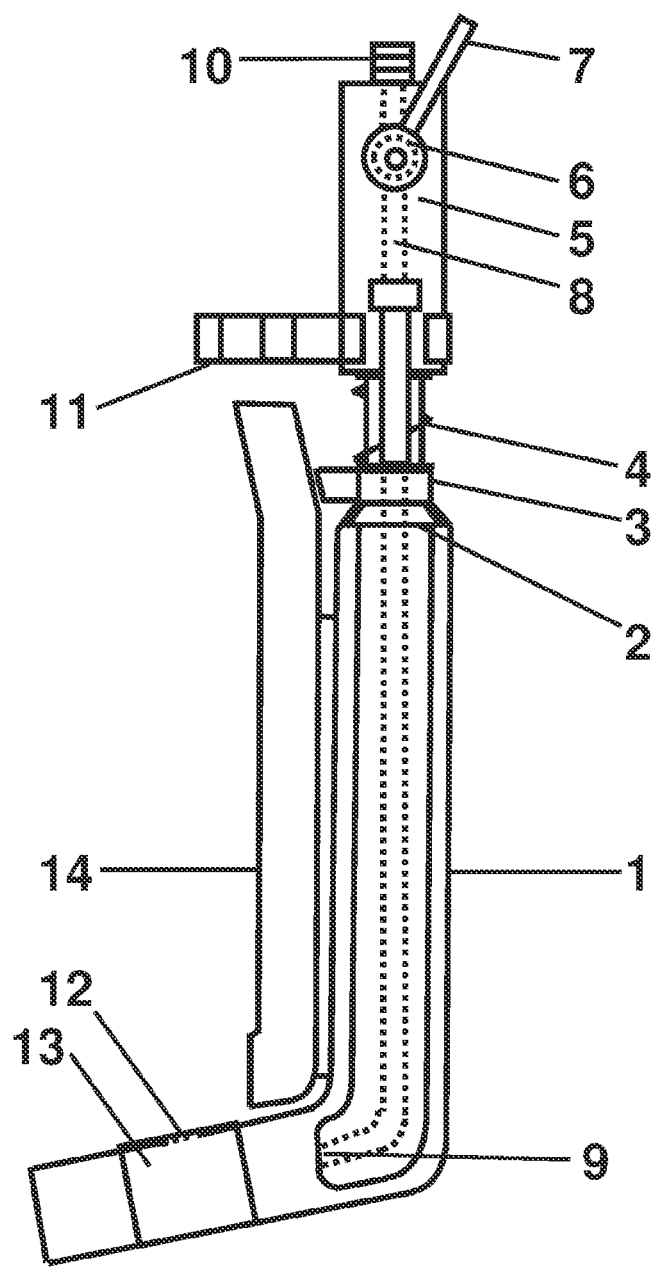
FIG. 1 shows a side view of a sanitary device with a transparent sanitary bag that can be filled with water and used for the surface washing of intimate body parts by gentle rubbing.

FIG. 1 shows a sanitary device with a transparent sanitary bag (1). The sanitary device includes a conical stop (2) with a ring (3) that is subjected to the action of a compression spring (4) to allow a tight holding of the sanitary bag (1) between the stop (2) and the ring (3), a valve (5) for controlling the flow of water, which is kept closed at rest by the action of a torsion spring (6) on a lever (7), a water passage (8), a water outlet (9), a thread (10) for coupling a water supply hose and an open ring (11) for holding a hot air supply hose. During the washing of the intimate body parts, the water flows out of a water outlet (12) of the sanitary bag (1), with the water outlet (12) being covered with a strip (13) that prevents splashing. The sanitary bag (1) includes a cylindrical part (14) which allows the flow of hot air coming from the outlet of the hot air supply hose to be directed toward the intimate body parts during drying. The ring (3) has an external projection that holds the part (14) around this outlet. The sanitary device can also be used for vaginal washing using a sanitary bag (15), for perineal rehabilitation and women's vaginal pleasure using a sanitary bag (16).

The valve (5), the internal part of which is not shown, is provided in a cavity of the water passage (8) of the sanitary device according to the well-known technique of ball valves where the obturator is spherical with a diametric water passage and placed between two seals. Rotating the lever (7) allows the alignment of the water passage of the spherical obturator with the water passage (8) and the opening of the valve.

Figure 2:
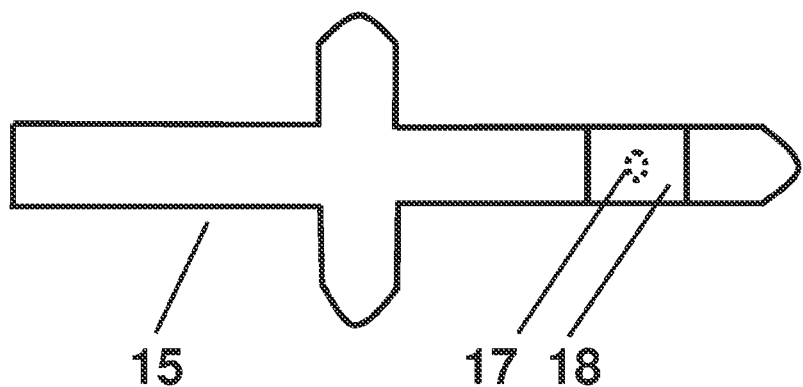
FIG. 2 shows a front view of a sanitary bag intended for vaginal washing.

FIG. 2 shows a front view of a sanitary bag (15) intended for vaginal washing, with a central part that is wider than the part intended for insertion of the free end of the sanitary device and the part that is shaped like a penis and can be introduced into the user's vagina. The central part limits the part that can be introduced into the user's vagina. The sanitary bag (15) has a water outlet (17) that is covered with a strip (18) to prevent splashing.

Figure 3:
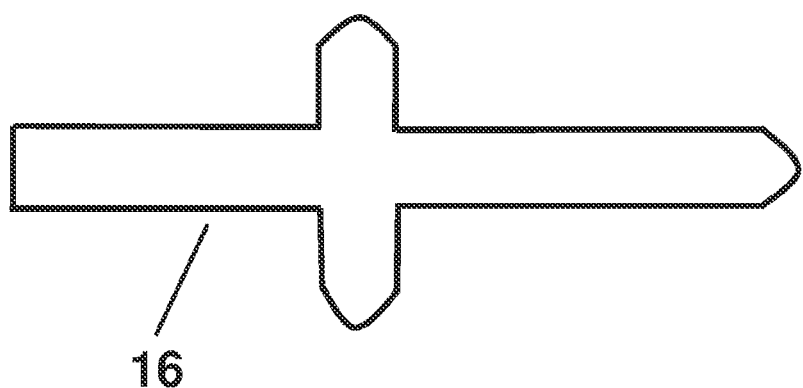
FIG. 3 shows a front view of a sanitary bag intended for perineal rehabilitation and women's vaginal pleasure.

FIG. 3 shows a front view of a sanitary bag (16) intended for perineal rehabilitation and women's vaginal pleasure. It has the same shape as the sanitary bag (15) but without the water outlet or the strip. The part which has the shape of a penis and which can be introduced into the vagina of the user can possibly be lubricated or covered with a lubricated condom before its use.

The sanitary bag (15) intended for vaginal washing and the sanitary bag (16) intended for perineal rehabilitation and women's vaginal pleasure can also be used with the washing bulb that is intended for portable use, a nut and a male/male union or a hose with a male union on each end. One of the threads of the union can be used with a nut for the tight holding of a sanitary bag (15) or (16) and the other can be screwed onto the washing bulb. If a hose is used, one of the unions can also be used with a nut for the tight holding of a hygiene bag (15) or (16) and the other can be screwed onto the washing bulb. For perineal rehabilitation and women's vaginal pleasure, the washing bulb can be filled with water at about 36° C. and the sanitary bag should be attached to this washing bulb by means of a union and a nut or a hose with a union on each end and a nut. Then the penis-shaped part of the sanitary bag (16) should be introduced into the user's vagina. Each time the washing bulb is squeezed, the sanitary bag (16) fills with water or air and becomes taut. This can cause vaginal pleasure for the user. In the case of perineal rehabilitation, the user must press alternately the washing bulb with her hand and the hygienic sachet (16) with the contraction of the muscles of her perineum while accompanying the return of water towards the washing bulb.

Figure 4:
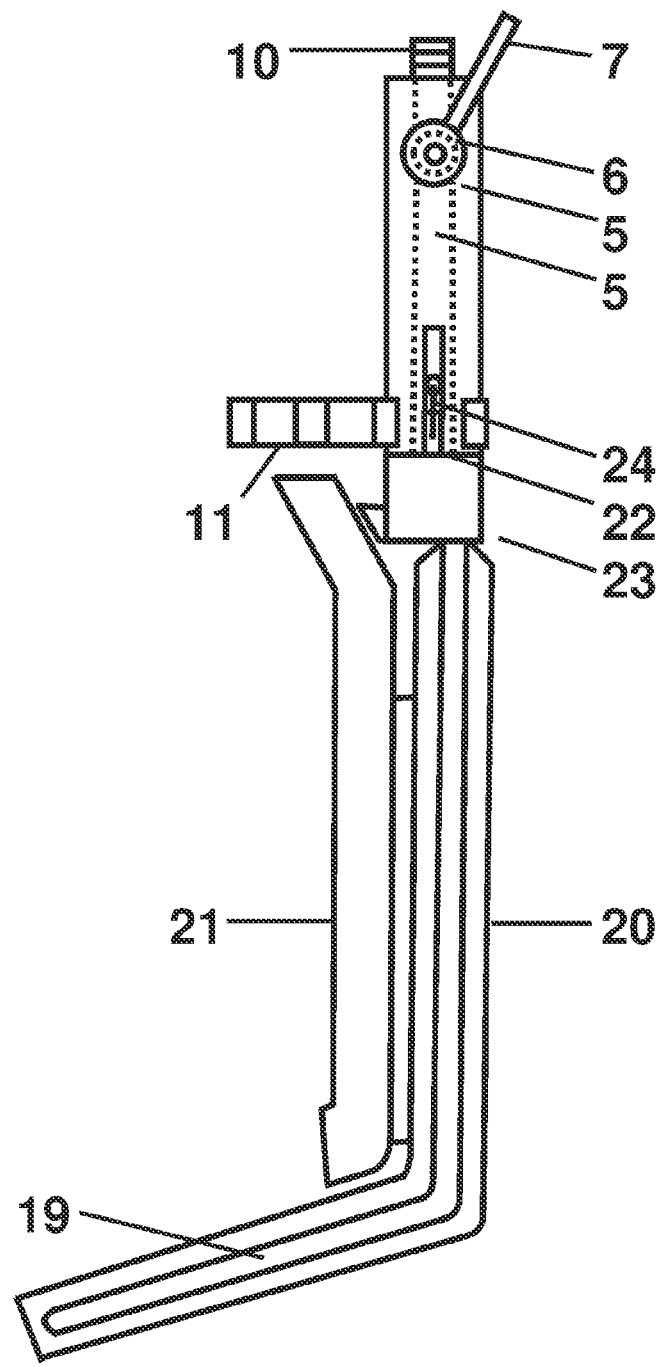
FIG. 4 shows a side view of a sanitary device with a smooth end that is covered with a transparent sanitary bag.

FIG. 4 shows a sanitary device for the surface washing of intimate body parts by gentle rubbing. It includes a smooth end (19) which is covered by a transparent sanitary bag (20) that includes a cylindrical part (21) which allows the flow of hot air to be directed toward the intimate body parts during drying and a water outlet (22) which allows a flow of water over this bag. A clip (23) which is held closed by a split elastic ring (24) holds the sanitary bag (20) and replaces the stop (2), the ring (3) and the compression spring (4). The rest of the device is identical to the one shown in FIG. 1.

Figure 5:
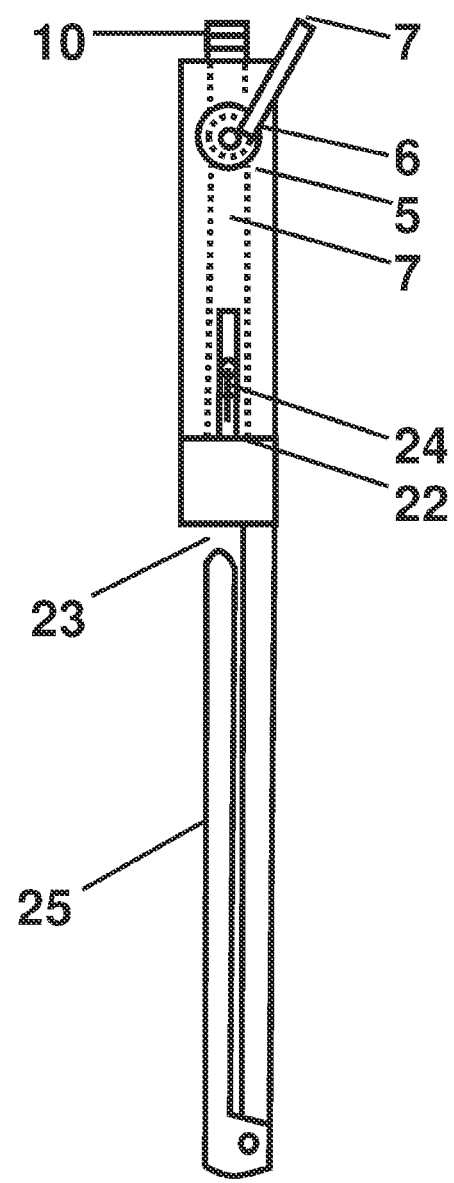
FIG. 5 shows a side view of a foldable and portable sanitary device.

FIG. 5 shows a sanitary device with a smooth bendable end (25) and without a ring for holding a possible hot air supply hose. The rest of the device is made in the same way as shown in FIG. 4.

To allow automatic opening of the power supply circuit of the dryer after the time preset on the timer, the normally closed contact of the timer is connected between a power supply conductor of the dryer and the normally open contact of the change-over contact of the pressure switch.

One power supply terminal of the timer is connected to the normally open contact of the change-over contact of the pressure switch and the other terminal is connected to a connection terminal that is shared by two power supply conductors: one from the dryer and the other from the instantaneous water heater.

The second power supply conductor of the instantaneous water heater is connected to the normally closed contact of the change-over contact of the pressure switch. The phase of the power supply network must be connected to the common contact of the change-over contact of the pressure switch and the neutral conductor must be connected to the connection terminal shared by the power supply conductors: of the dryer, of the instantaneous water heater and of the timer.

The pressure switch is screwed onto a T-fitting to allow coupling of the other hydraulic components of the instantaneous water heater. The order of coupling of these components does not significantly affect the operation of the water heater and dryer. When opening the valve (5), the water pressure in the pressure switch decreases and the change-over contact switches the phase of the power supply network of the dryer and the timer which are connected in parallel to the instantaneous water heater, to allow the water to be heated. When closing the valve (5), the water pressure in the pressure switch returns to its initial value and the change-over contact also returns to its initial position, switching the power supply from the instantaneous water heater to the dryer and timer. The operating time of the dryer corresponds to the time set on the timer.

To minimize the time required for drying, the side parts of the sanitary bag (1) filled with water can be used to wipe the intimate body parts after each wash. If a sanitary device with a smooth end (19) is used, the intimate body parts can be wiped with this end (19) covered with a sanitary bag (20) after each wash. The sanitary bags (1,15,16,20) are made of an impermeable, essentially biodegradable and compostable material.

The sanitary device according to the invention is particularly intended for the surface washing of intimate body parts, vaginal washing, rehabilitation of the perineum and women's vaginal pleasure with using the sanitary bag provided for each use.

The invention claimed is:

1. A hand-held sanitary device and sanitary bag for washing and drying intimate body parts, wherein the hand-held sanitary device includes a conical stop with a first ring that is subjected to an action of a compression spring to allow a tight holding of the sanitary bag that is filled with water so as to be used for rubbing intimate body parts during washing and that includes a cylindrical part that allows a flow of hot air to be directed toward the intimate body parts during drying, a water flow control valve for controlling a flow of water, a water passage, a water outlet, a thread for coupling a water supply hose and a second ring for holding a hot air supply hose.

2. A hand-held sanitary device as well as a sanitary bag for washing and drying intimate parts, wherein the hand-held sanitary device includes a conical stop with a first ring that is subjected to an action of a compression spring to allow a tight holding of the sanitary bag that is filled with water so as to be used for rubbing intimate body parts during washing and that includes a cylindrical part that allows a flow of hot air to be directed toward the intimate body parts during drying, a water flow control valve for controlling a flow of water, a water passage, a water outlet, a thread for coupling a water supply hose and a second ring for holding a hot air supply hose, wherein the hand-held sanitary device includes a smooth end configured for a surface rubbing of the intimate body parts during washing with covering the smooth end with the sanitary bag that has a cylindrical part that allows to direct the flow of hot air toward the intimate body parts during drying, a water outlet and a clip that is kept closed by a split elastic ring.

3. A hand-held sanitary device as well as a sanitary bag for washing and drying intimate parts, wherein the hand-held sanitary device includes a conical stop with a first ring that is subjected to an action of a compression spring to allow a tight holding of the sanitary bag that is filled with water so as to be used for rubbing intimate body parts during washing and that includes a cylindrical part that allows a flow of hot air to be directed toward the intimate body parts during drying, a water flow control valve for controlling a flow of water, a water passage, a water outlet, a thread for coupling a water supply hose and a second ring for holding a hot air supply hose, wherein the hand-held sanitary device includes a smooth end configured for a surface rubbing of the intimate body parts during washing with covering the smooth end with the sanitary bag that has a cylindrical part that allows to direct the flow of hot air toward the intimate body parts during drying, a water outlet and a clip that is kept closed by a split elastic ring, wherein the hand-held sanitary device includes a foldable smooth end which facilitates transport of the hand-held sanitary device for use with a water container which is intended for portable uses.

4. The hand-held sanitary device according to claim 1, wherein the hand-held sanitary device is configured to be supplied with hot water and hot air by an instantaneous water heater and dryer which includes a pressure switch with an electric change-over contact that switches a power supply between the instantaneous water heater and the dryer by opening or closing the water flow control valve, a pressure reducer which limits a water pressure in the water supply hose and in the sanitary bag which fills up with water when washing the intimate body parts and a timer which allows to set a duration of hot air drying of the intimate body parts after each wash.

5. The hand-held sanitary device according to claim 2, wherein the hand-held sanitary device is configured to be supplied with hot water and hot air by an instantaneous water heater and dryer which includes a pressure switch with an electric change-over contact that switches a power supply between the instantaneous water heater and the dryer by opening or closing the water flow control valve, a pressure reducer which limits a water pressure in the water supply hose and in the sanitary bag which fills up with water when washing the intimate body parts and a timer which allows to set a duration of hot air drying of the intimate body parts after each wash.

6. The hand-held sanitary device according to claim 1, wherein the water flow control valve is kept closed at rest by an action of a torsion spring on a lever.

\* \* \* \* \*